(12) United States Patent
Sansom

(10) Patent No.: US 6,745,800 B1
(45) Date of Patent: Jun. 8, 2004

(54) ARRANGEMENT FOR PREVENTING OVERFILL OF ANESTHETIC LIQUID

(75) Inventor: Gordon G. Sansom, Scaniport Inverness (GB)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/654,791

(22) Filed: Sep. 4, 2003

(51) Int. Cl.$^7$ .................................................. B65B 1/30
(52) U.S. Cl. ................................ 141/198; 128/200.19
(58) Field of Search .................. 141/198, 95; 137/122, 137/409, 4; 128/200.14–200.23

(56) References Cited

U.S. PATENT DOCUMENTS

| | | | | |
|---|---|---|---|---|
| 2,244,986 A | * | 6/1941 | Drane .......................... | 137/122 |
| 2,340,936 A | * | 2/1944 | Cook .......................... | 137/386 |
| 4,715,370 A | | 12/1987 | Altner et al. .......... | 128/204.13 |
| 5,144,991 A | | 9/1992 | Wallroth et al. ............. | 141/192 |
| 5,381,838 A | * | 1/1995 | Watanabe et al. ........... | 141/198 |
| 5,470,511 A | | 11/1995 | Laybourne et al. ........... | 261/55 |
| 5,474,112 A | | 12/1995 | Carola ............................ | 141/7 |
| 5,478,506 A | | 12/1995 | Lavimodiere ............... | 261/72.1 |
| 5,611,375 A | | 3/1997 | Kankkunen et al. .......... | 141/18 |
| 5,904,188 A | | 5/1999 | Heinonen et al. .............. | 141/18 |
| 6,138,672 A | | 10/2000 | Kankkunen ............ | 128/203.12 |
| 6,585,016 B1 | | 7/2003 | Falligant et al. ............ | 141/352 |

* cited by examiner

Primary Examiner—Steven O. Douglas
(74) Attorney, Agent, or Firm—Andrus, Sceales, Starke & Sawall, LLP

(57) ABSTRACT

A filling system for use between an anesthetic storage container and a drug reservoir of an anesthetic vaporizer to prevent overfilling of the drug reservoir. The filling system includes a filling conduit that extends between the drug reservoir and the anesthetic storage container to allow a liquid anesthetic agent to flow from the storage container to the drug reservoir. A closing valve is positioned adjacent to a flow opening of a filling conduit such that the closing valve can be moved to a closed position to prevent the flow of anesthetic agent into the drug reservoir. The closing valve includes a float that controls the opening and closing of the closing valve depending upon the level of the anesthetic agent within the drug reservoir.

13 Claims, 6 Drawing Sheets

ARRANGEMENT FOR PREVENTING OVERFILL OF ANESTHETIC LIQUID

BACKGROUND OF THE INVENTION

The present invention generally relates to an arrangement for the overfill protection for a container of anesthetic liquid being transferred to a drug reservoir for an anesthetic vaporizer. More specifically, the present invention relates to an overfill protection device that prevents the overfilling of the drug reservoir of a vaporizer for use specifically with an anesthetic liquid having a low boiling point. The filling arrangement prevents the overfill of the drug reservoir due to the increased pressure within the anesthetic liquid storage container relative to the supply of anesthetic liquid contained within the drug reservoir.

During the supply of anesthesia, the gaseous anesthetic agent inhaled by the patient is formed of oxygen, nitrogen, nitrous oxide and an inhalation anesthetic agent. Inhalation anesthetics are typically in liquid form at administration temperatures, and an anesthetic vaporizer is needed to gasify the liquid. Anesthetic vaporizers have a drug reservoir for storing the supply of the agent to be vaporized. The vaporized anesthetic is administered for the patient to inhale by means of a carrier gas flow.

Vaporizer reservoirs are provided with fill conduits and valves by way of which inhalation liquids may be added to the container or, when necessary, drained therefrom. Liquid is added to the vaporizer reservoir by either a filling device that is specifically designed for the anesthetic agent or by directly pouring the anesthetic agent into a filling hopper. It is a characteristic of the filling device that it can only be fixed to the storage container for a desired, single type of an anesthetic liquid to be transferred to the vaporizer. Such filling device is characterized and shown in U.S. Pat. No. 6,585,016, the disclosure of which is incorporated herein by reference.

The filling device, such as shown in the above-identified patent, incorporates a liquid flow conduit and a gas flow conduit. The filling of the drug reservoir for the anesthetic vaporizer is based on the exchange of volume in the vaporizer and the storage container for the anesthetic liquid. When the anesthetic liquid flows into the vaporizer, an equivalent volume of gas flows out of the vaporizer and back into the storage container. Correspondingly, when liquid flows out of the storage container, an equivalent volume of gas flows into it. Typically, the filling of the vaporizer stops if the replacement gas flow is exhausted or blocked.

It is essential for the operation of the vaporizer that the vaporizer drug reservoir is not filled over a maximum limit. If the vaporizer reservoir is overfilled, the result may be that an overly high dose of anesthetic agent is delivered, which may, in the worst case, rapidly cause death. Otherwise, depending upon the vaporizer, the vaporizer may stop vaporizing, which would cause the patient to awaken too early.

Referring to FIGS. 1 and 2, thereshown is a typical filling arrangement between a drug reservoir 10 for an anesthetic vaporizer and a container 12 containing a supply 14 of an anesthetic agent. As illustrated in FIG. 1, a filler 16 is positioned between the container 12 and the drug reservoir 10 to provide a conduit between the container 12 and the open interior 18 of the reservoir 10. In the prior art embodiment shown in FIGS. 1 and 2, the filling system is closed and the anesthetic liquid 14 is not allowed to vaporize to external atmosphere. The filler 16 includes a liquid tube 20 extending from the storage container 12 to the open interior 18 of the reservoir 10. A gas tube 22 also extends from the container 12 to the open interior 18 of the drug reservoir 10.

As illustrated in FIG. 1, when the anesthetic vapor from within the open interior 18 is withdrawn through the discharge tube 24 of the vaporizer and administered to the patient, the level of the anesthetic agent 26 falls below the inlet end 28 of the gas tube 22. Since the supply of anesthetic agent 14 contained within the storage container 12 is typically at the same pressure as the anesthetic agent 26 within the reservoir 18, gas travels from the drug reservoir 18 through the gas tube 22 and displaces the anesthetic agent 14 from within the storage container 12 through the liquid tube 20. This process continues until the level of the anesthetic agent 26 within the open interior 18 rises above the inlet end 28 of the gas tube 22. When the inlet end 28 is covered, no additional gas can flow back to the storage container 12 and filling of the drug reservoir 10 is halted. As can be seen in FIG. 2, the inlet end 28 of the gas tube 22 is well below the inlet end 30 of the discharge tube 22 to prevent the flow of the anesthetic agent 26 directly into the discharge tube 24.

Presently, the filler 16 includes either keyed elements or a color coding to insure that only a desired type of anesthetic agent is used with the filling arrangement. Thus, the storage container 12 can be connected only to a filling device suitable for the particular anesthetic agent being delivered.

Unlike many other anesthetic agents, Desflurane boils at room temperature. When the anesthetic liquid begins to boil, the pressure inside the storage container 12 increases. If the temperature of the anesthetic agent 14 in the storage container 12 exceeds the temperature of the anesthetic agent 26 contained within the drug reservoir, the pressure in the storage container 12 can cause the level of the anesthetic agent 26 within the reservoir 10 to continue to rise even though the inlet end 28 of the gas tube is covered and no vapor is flowing back into the supply container 12. In the worst case, the pressure of the Desflurane contained within the storage container 12 may cause the level of the anesthetic agent within the drug reservoir 10 to flow to the dosing device, thus causing malfunction in the entire anesthesia device. Therefore, a need exists for an arrangement for preventing the overflow of an anesthetic liquid into the liquid container of an anesthetic vaporizer, particularly when the anesthetic agent has a low boiling point.

SUMMARY OF THE INVENTION

The present invention is a filling system for use between an anesthetic storage container and an anesthetic vaporizer having a drug reservoir. The filling system of the present invention is useful in transferring a liquid anesthetic agent between the anesthetic storage container and the drug reservoir.

The filling system includes a filling device that is positioned between the drug reservoir for the vaporizer and the anesthetic storage container. The filling device includes at least one filling conduit that allows the liquid anesthetic agent to pass from the anesthetic storage container to the drug reservoir. Additionally, the filling conduit allows a flow of replenishment gas to pass from the drug reservoir back into the anesthetic storage container.

The filling conduit includes a filling opening that allows the filling conduit to empty into the drug reservoir. The filling opening provides the lone passageway for both the anesthetic agent and replenishment gas to pass between the storage container and the drug reservoir.

The filling system of the present invention includes a closing valve that is operatively positioned adjacent to the flow opening and is movable between an open position and a closed position. When the closing valve is in the closed position, the closing valve prevents the flow of the anesthetic liquid from the anesthetic storage container into the drug reservoir. The closing valve is configured to move between the open and closed positions based on the level of the anesthetic agent within the drug reservoir. Thus, the closing valve controls the flow of anesthetic agent based upon the amount of anesthetic agent within the drug reservoir, rather than based upon the flow of replacement gas between the anesthetic agent in the anesthetic storage container and the drug reservoir.

The closing valve of the present invention includes a float that is freely movable as the level of the anesthetic agent rises and falls within the drug reservoir. Specifically, the float is pivotally mounted to a wall of the drug reservoir such that as the drug level rises, the float pivots both upward and away from the flow opening.

The closing valve includes a support shaft that is mounted to the float and extends through the flow opening. The support shaft includes an expanded head and a sealing ring. When the float rises with the level of anesthetic agent within the drug reservoir, the sealing ring covers the flow opening and prevents the flow of any additional anesthetic agent into the drug reservoir when the level of the anesthetic in the drug reservoir reaches a desired level. As the anesthetic agent is withdrawn from the drug reservoir, the level of the anesthetic agent decreases and the float pivots downward and toward the flow opening to move the sealing ring away from the flow opening. As the sealing ring moves away from the flow opening, anesthetic agent is again allowed to flow into the drug reservoir.

One advantage of the present invention is the ability of the filling system to prevent the overfilling of the drug reservoir, particularly when the drug reservoir is being used with an anesthetic agent having a low boiling point, such as Desflurane. The filling system of the present invention relies upon the level of the liquid in the drug reservoir to open and close a valve, rather than relying upon the flow of a replacement gas. The closing valve eliminates the potential danger caused by the pressure differential between the anesthetic agent within a storage container and the anesthetic agent within the drug reservoir. The arrangement thus prevents overfilling when there is a temperature difference between the anesthetic storage container and the drug reservoir.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 3:
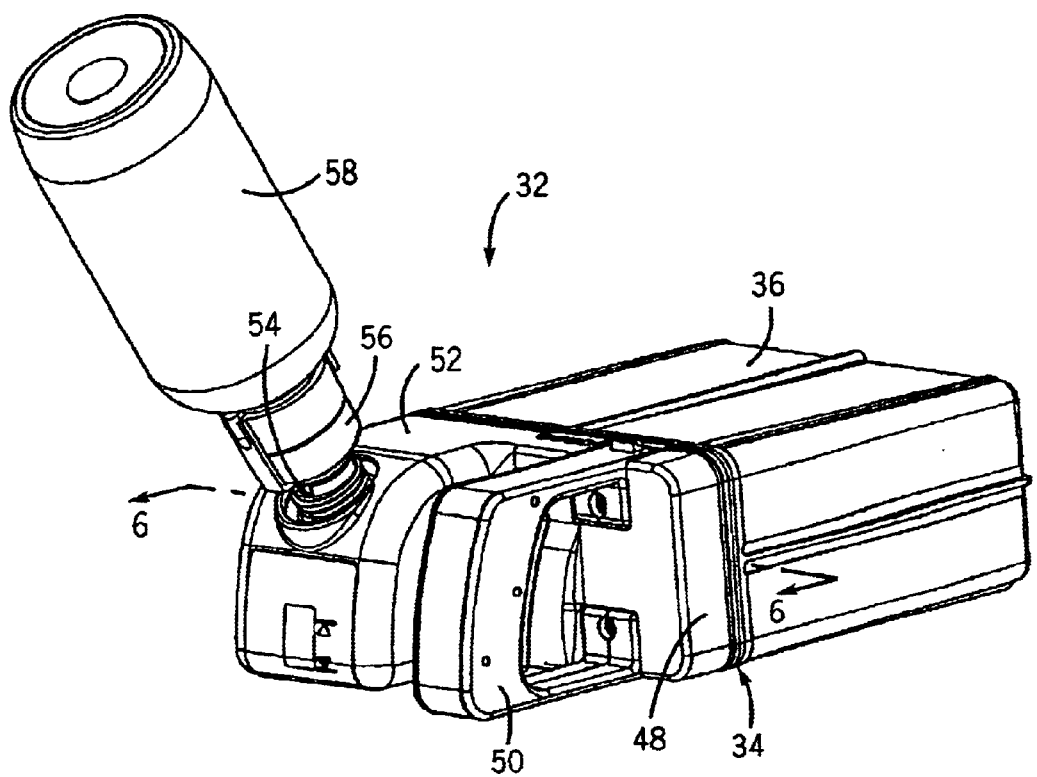
FIG. 3 is a perspective view illustrating a cassette-type filling arrangement of the present invention.

Referring first to FIG. 3, thereshown is the filling system 32 of the present invention. The filling system 32 is shown as being incorporated in a cassette 34, such as the Aladin model available from Datex-Ohmeda, Inc., Madison, Wis. The cassette 34 is removable from the vaporizer (now shown) such that a supply of an anesthetic agent can be delivered to a patient by the vaporizer. The cassette 34 is removable from the vaporizer such that different types of anesthetic agents can be supplied to the vaporizer by simply removing the cassette 34 and replacing it with a different cassette for a different anesthetic agent. Throughout the preferred embodiment of the invention, the cassette 34 will be discussed as being useful with a particular anesthetic agent, namely Desflurane, although it should be understood that the filling system and cassette could be utilized with other types of anesthetic agent while operating within the scope of the present invention.

Figure 4:
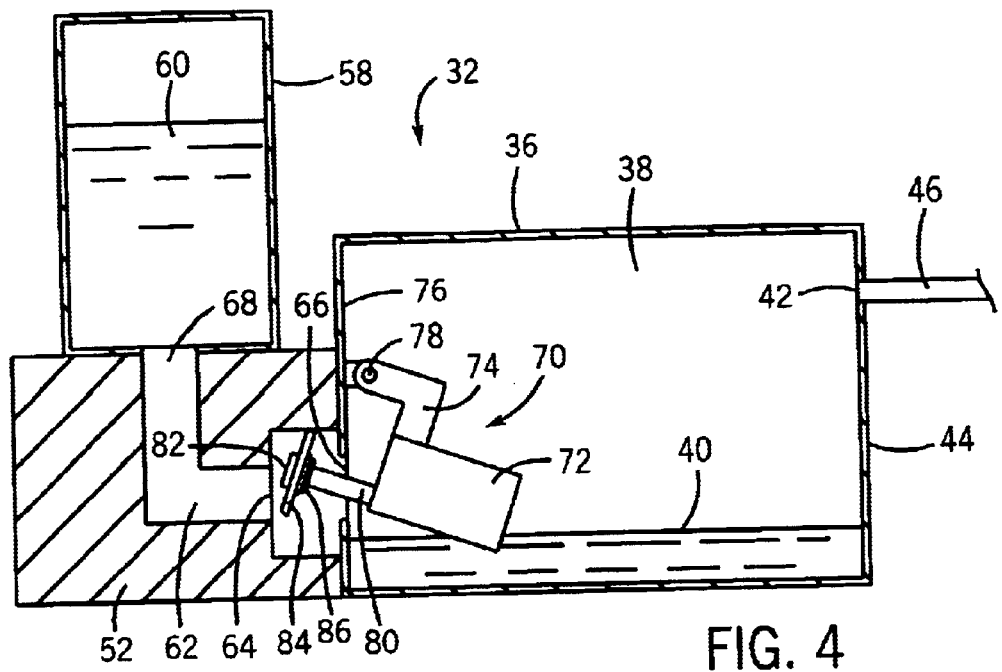
FIG. 4 is a schematic side view of the filling arrangement of the present invention illustrating the filling arrangement in an open position.

The cassette 34 generally includes a drug reservoir 36 that contains a supply of anesthetic agent to be delivered to a patient The drug reservoir 36, as illustrated schematically in FIG. 4, includes an open interior 38 that receives a stored supply of anesthetic agent 40. The drug reservoir 36 has a discharge opening 42 formed in the back wall 44 that receives a discharge tube 46 formed as part of the vaporizer. Typically, the reservoir 36 plugs into the vaporizer such that the discharge tube 46 is received within the discharge opening 42 and forms a gas-tight seal for the delivery of anesthetic vapor to a patient.

Referring back to FIG. 3, the cassette 34 includes a front cover 48 including a handle 50. The front cover encloses a filling device 52 having a filler port 54. The configuration of the filling device and filling port of the preferred embodiment of the invention are disclosed in U.S. Pat. No. 6,585,016, the disclosure of which is incorporated herein by reference.

As illustrated in FIG. 3, the filler port 54 receives a bottle adapter 56 on the anesthetic storage container 58. As discussed previously, in the preferred embodiment of the invention, the anesthetic storage container 58 includes a supply of an anesthetic liquid, namely Desflurane. The interaction between the bottle adapter 56 and the filler port 54 allows only a single type of anesthetic agent to be dispensed into the drug reservoir 36 of the cassette 34. A different cassette 34, including a specific filler port 54, is required for dispensing each different type of anesthetic agent. In this manner, the improper delivery of an anesthetic agent can be eliminated.

Figure 1:
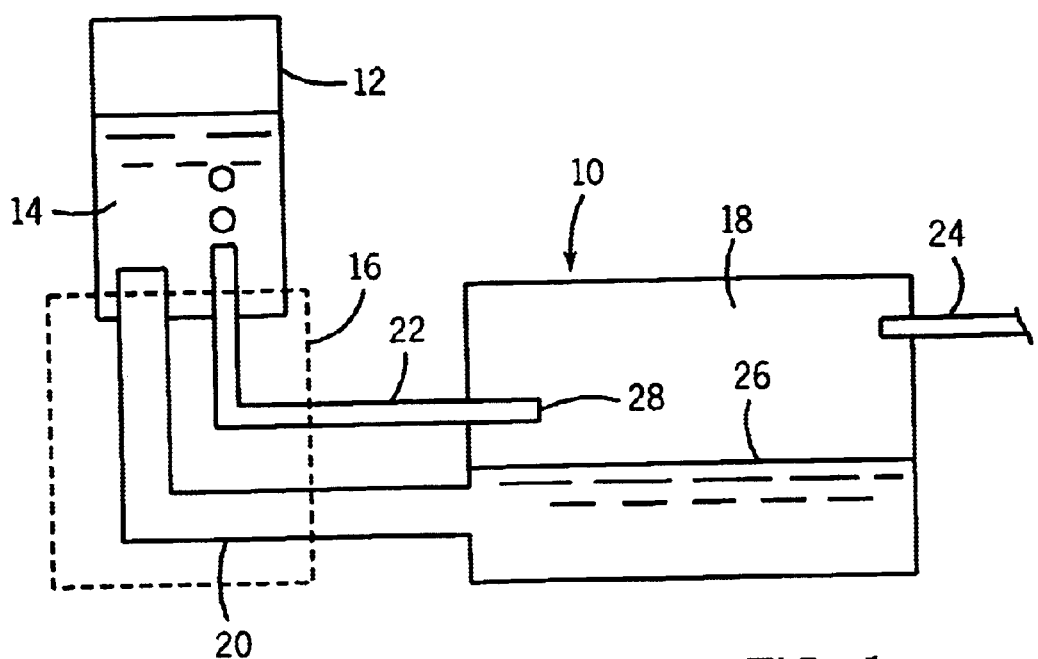
FIG. 1 is a schematic illustration of a prior art filling arrangement between a drug reservoir of an anesthetic vaporizer and a storage container of an anesthetic agent.
Figure 5:
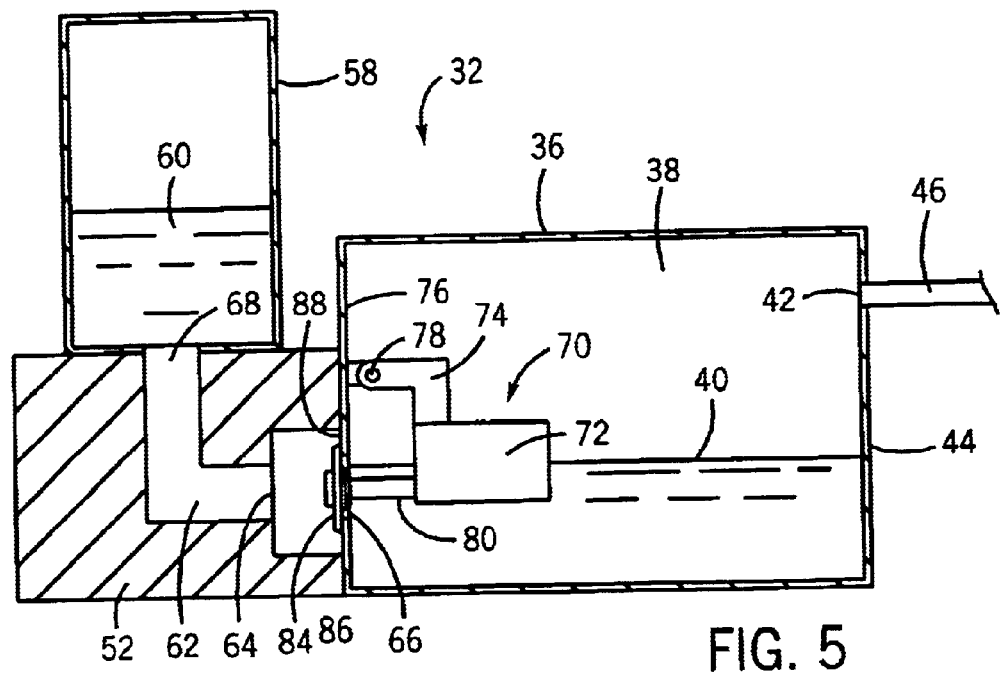
FIG. 5 is a view similar to FIG. 4 illustrating the filling arrangement in a closed position.

Referring now to FIGS. 4 and 5, thereshown is a schematic illustration of the filling system of the present invention. As discussed previously, the filling system shown in FIGS. 1 and 2 work properly for most conventional anesthetic drugs, such as Enflurane, Halothane, Isoflurane and Sevoflurane. For these typical anesthetic agents, the pressure difference over a small temperature change is relatively small. For example, the pressure rise of Sevoflurane from 21° C. to 23° C. is approximately 15 mmHg. Thus, if the storage container 12 shown in FIG. 1 is at a slightly higher temperature than the supply of anesthetic agent 26 within the open interior 18 of the drug reservoir, the pressure difference between the two containers is very slight.

Figure 2:
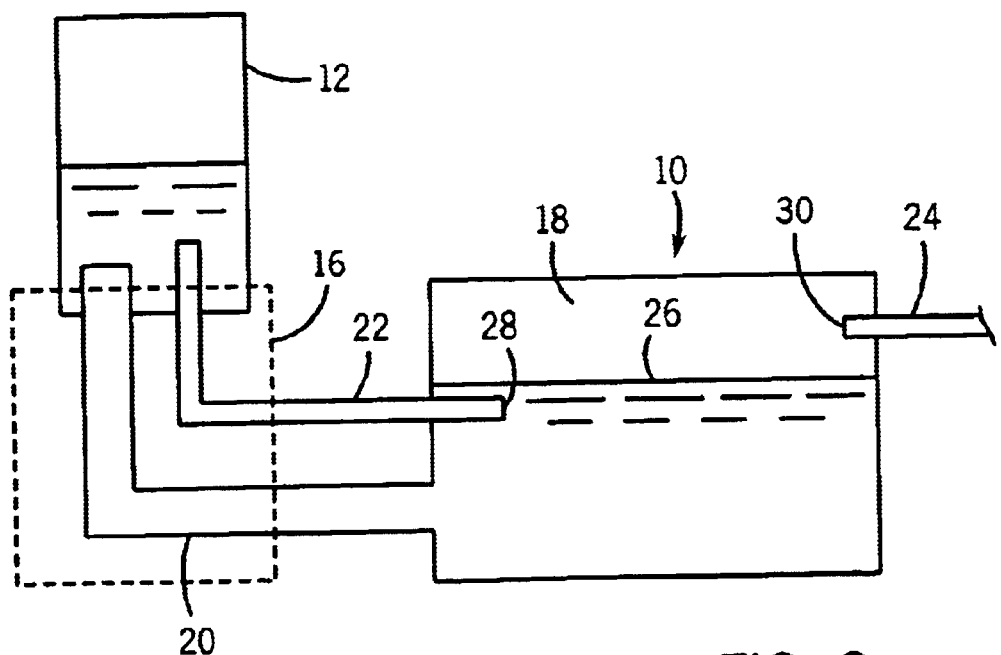
FIG. 2 is a schematic view similar to FIG. 1 showing the operation of the prior art filling arrangement to prevent the overflow of the anesthetic vaporizer when using an anesthetic agent having a high boiling point.

However, in the case of the anesthetic agent Desflurane, the pressure difference for a small temperature change is much larger due to the low boiling point of the liquid. As an example, the pressure rise of Desflurane for a temperature change from 21° C. to 23° C. is approximately 65 mmHg, which is more than four times greater than Sevoflurane. As discussed previously, if the temperature of the supply of anesthetic agent 14 in the storage container 12 is slightly greater than the temperature of the anesthetic agent 26 within the open interior 18, the pressure difference can cause the level of the anesthetic agent in the liquid container 18 to rise above the inlet end 28 of the gas tube 22, as illustrated in FIG. 2. If the pressure differential is great enough, the liquid level can rise to the discharge opening 30 of the delivery tube 24, which could result in an overdose of anesthetic to a patient. Based upon this characteristic of Desflurane, the filling system 32 of the present invention has been developed.

Referring back to FIG. 4, the anesthetic storage container 58 is shown including a supply 60 of an anesthetic agent, such as Desflurane. The storage container 58 is shown mounted to the filling device 52, which in turn is attached to the drug reservoir 36. As illustrated in FIG. 4, the filling device 52 includes a single filling conduit 62 that provides a flow passageway for both liquid and vapor to pass from the storage container 58 to the drug reservoir 36. The filling conduit 62 extends from a first end 64 having a filling opening 66 in communication with the open interior 38 of the drug reservoir 36 to a second end 68 in communication with the open interior of the anesthetic storage container 58. The filling conduit 62 provides a passageway for both the liquid anesthetic agent and the replenishment gas to flow between the anesthetic storage container 58 and the drug reservoir 36.

The filling system 32 of the present invention includes a closing valve 70 that is positioned adjacent to the flow opening 66 of the filling conduit 62 to selectively cover the flow opening 66 and prevent the flow of both gases and liquid between the drug reservoir 36 and the anesthetic storage container 58. The closing valve 70 is movable in direct response to the changing level of the anesthetic agent 40 contained within the open interior of the drug reservoir 36. When the level of the anesthetic agent 40 reaches a desired level, the closing valve 70 blocks the flow opening 66 to prevent any additional anesthetic agent from flowing into the open interior 38 of the drug reservoir 36. Thus, the closing valve 70 eliminates the possibility of overfilling the drug reservoir 36 if the pressure of the anesthetic agent 60 contained within the anesthetic storage container 58 exceeds the pressure of the drug reservoir 36 due to a temperature differential between the anesthetic agent in the storage container 58 and the drug reservoir 36.

Referring back to FIG. 4, the closing valve 70 generally includes a float 72 contained within the open interior 38 and resting within the stored supply of anesthetic agent 40. The float 72 includes a pair of pivot arms 74 that are each connected to an inner wall 76 by a pivot point 78. The float 72 is allowed to pivot about the point such that the float 72 can rise and fall along with the level of the anesthetic agent 40 contained within the reservoir 36.

The closing member 70 further includes a support shaft 80 mounted to the float 72. The support shaft 80 extends through the flow opening 66 and includes an expanded head 82. The expanded head 82 holds a resilient sealing ring 84 in place between the head 82 and a locking ring 86. As illustrated in FIG. 4, when the closing valve 70 is in an open position, the sealing ring 84 is spaced from the flow opening 66 such that both the anesthetic liquid and replenishment gas can flow freely between the storage container 58 and the drug reservoir 36. In the open position, the flow of both the anesthetic liquid and replenishment gas is controlled by the flow of the replenishment gas between the anesthetic storage container 58 and the drug reservoir 36, as was the case in the prior art system of FIGS. 1 and 2.

Referring now to FIG. 5, as the level of the anesthetic agent 40 in the drug reservoir 36 increases, the float 72 rises and pivots about the pivot point 78. The pivot arm 74 is specifically configured such that as the float pivots about point 78, the float 72 moves both upward and away from the flow opening 66. As the closing valve 70 pivots, the sealing ring 84 is brought into contact with the outer surface 88 of the inner wall 76 and blocks the flow opening 66. When the sealing ring 84 is engaged as shown, the level of the anesthetic agent 40 within the open interior 38 of the drug reservoir 36 cannot rise any further, regardless of the pressure contained within the anesthetic storage container 58. Thus, the filling system of the present invention limits the flow of the liquid anesthetic agent based upon the level of the liquid within the drug reservoir 36, regardless of the pressure differential between the drug reservoir 36 and the anesthetic storage container. Thus, the filling system of the present invention is particularly useful with anesthetic agents, such as Desflurane, that can have a significant pressure difference depending upon the difference between the temperatures of the agent.

In the preferred embodiment of the invention illustrated in FIGS. 4 and 5, the sealing ring 84 blocks the flow opening 66 just after the level of the anesthetic agent 40 contained within the open interior 38 rises above the upper edge of the flow opening 66. Thus, during normal operating conditions, the flow of the anesthetic agent is controlled by the availability of the replenishment gas to flow between the open interior 38 and the storage container 58, as was the case in the prior art system of FIGS. 1 and 2. However, if the pressure of the anesthetic agent 60 contained within the storage container 58 is elevated relative to the agent in the drug reservoir due to the low boiling point of the anesthetic agent, the sealing ring 84 will prevent additional flow of the anesthetic agent above a selected level. Thus, the filling system of the present invention is particularly useful with an anesthetic agent having a low boiling point, but also can be utilized in a conventional manner with other types of anesthetic agent.

Figure 6:
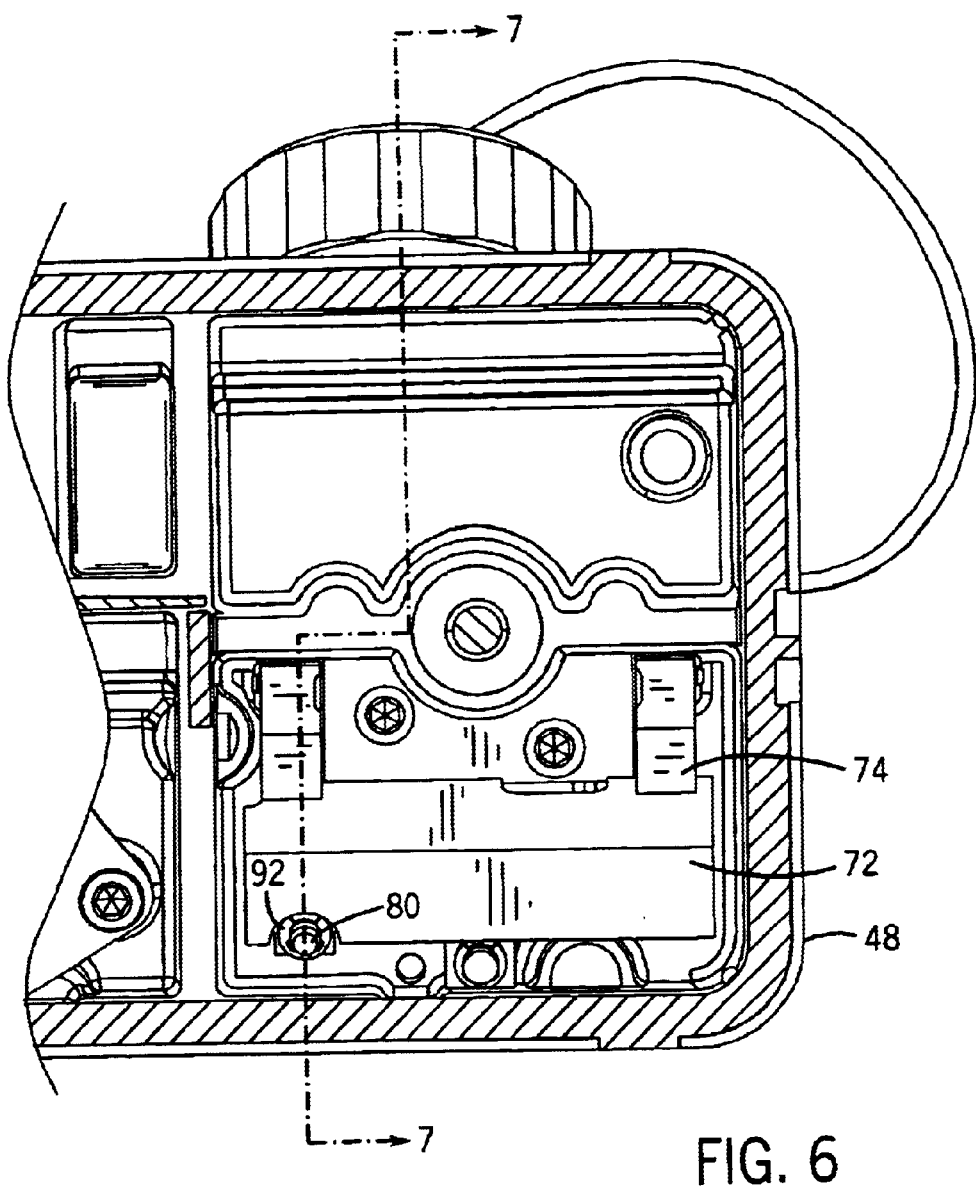
FIG. 6 is a partial section view taken along line 6—6 of FIG. 3.
Figure 7:
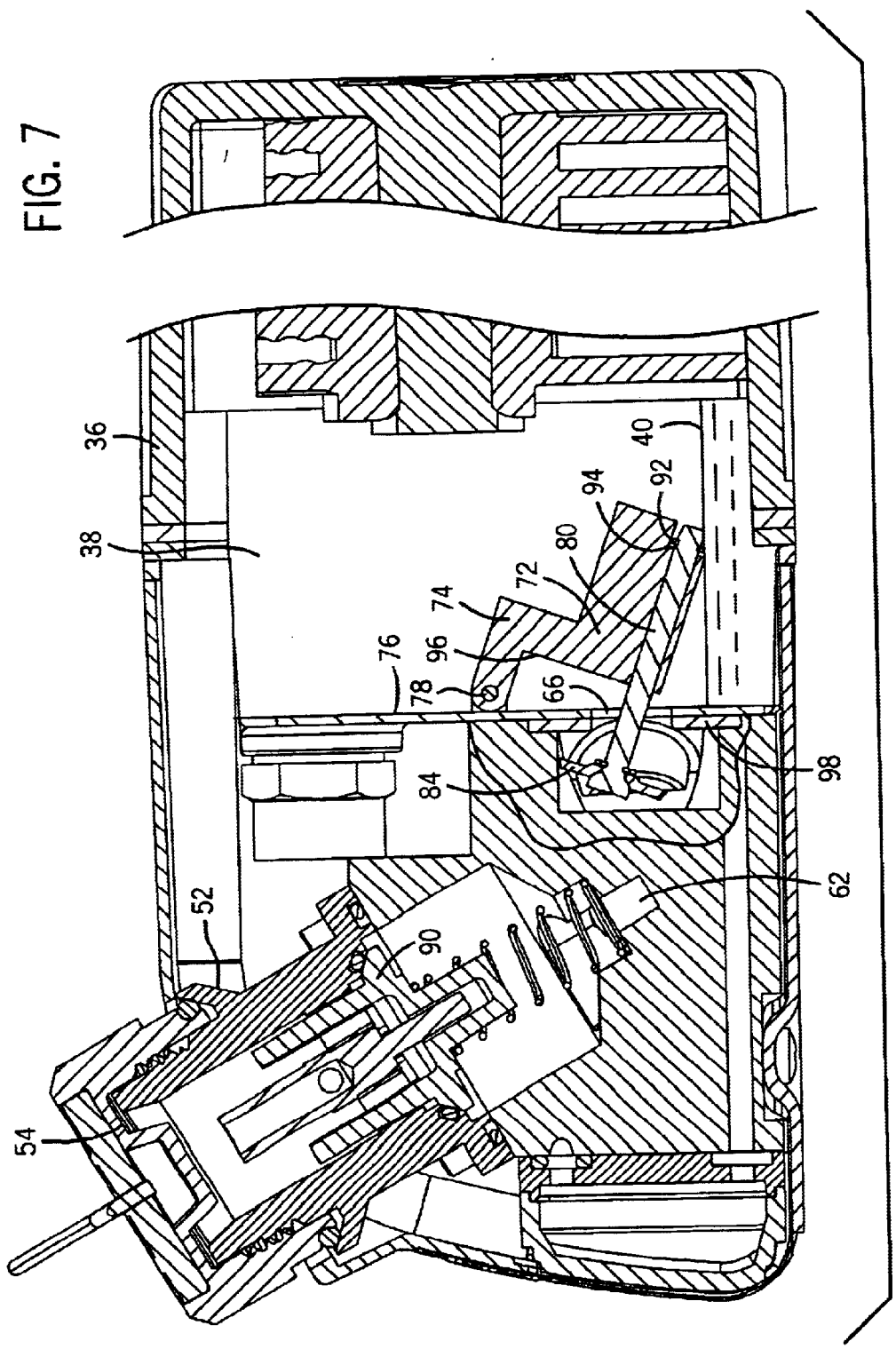
FIG. 7 is a section view taken along line 7—7 of FIG. 6.
Figure 8:
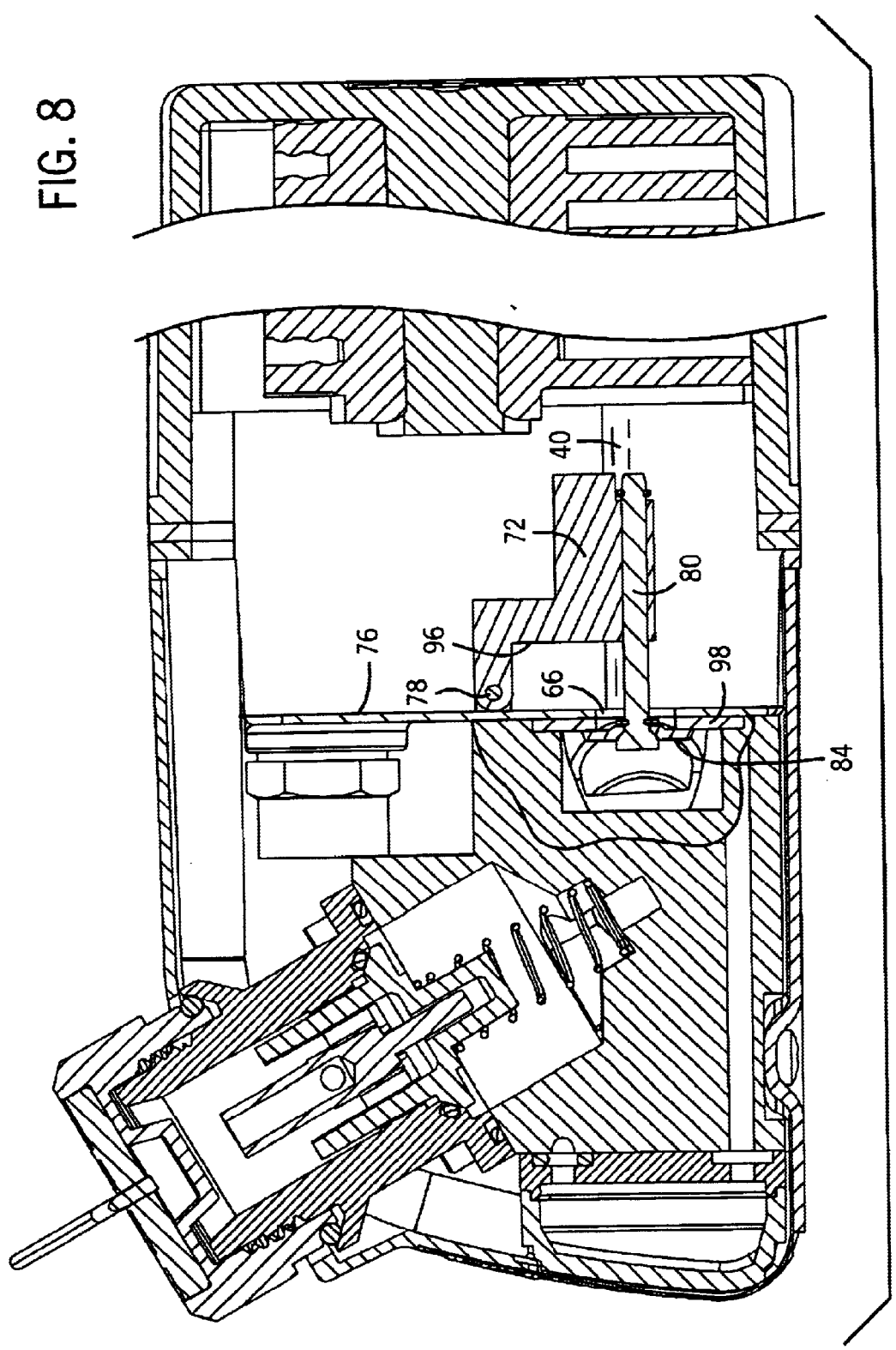
FIG. 8 is a section view similar to FIG. 7 showing the filling arrangement in a closed position.

Referring now to FIGS. 6–8, thereshown is an actual embodiment of the filling system of the present invention as compared to the schematic illustration of FIGS. 4–5. Referring first to FIG. 7, the filling device 52 includes an internal valve member 90 that allows the anesthetic agent to flow from the filler port 54 into the filling conduit 62 and ultimately to the flow opening 66. As illustrated in FIG. 7, the support shaft 80 extends through the body of the float 72 and includes a locking ring 92 that engages a shoulder 94. As can be understood in FIG. 7, the support shaft 80 can be slid into and out of the float 72 and the position of the locking ring 92 adjusted such that the length of the support shaft 80 extending from the face 96 of the float 72 can be adjusted. Thus, by adjusting the length of the support shaft 80 extending from the face 96 of the float 72, the desired level of the anesthetic agent 40 in the open interior 38 required before the sealing ring 84 contacts and engages the inner surface of the wall 76 to seal the flow opening 66 can be adjusted.

As shown in FIGS. 7 and 8, the inside surface of the wall 76 preferably includes a resilient sealing member 98. The sealing member 98 surrounds the flow opening 66 and provides a point of contact for the sealing ring 84, as shown in FIG. 8. The interaction between the sealing ring 84 and the sealing member 98 provides a liquid-tight seal for the flow opening 66.

Referring now to FIG. 6, the float 72 is mounted by the pair of pivot arms 74 to the reservoir cover 48 and is thus removable along with the reservoir cover 48. As shown in FIG. 6, the locking ring 92 surrounds the support shaft 80 to securely attach the support rod 80 to the float 72.

Various alternatives and embodiments are contemplated as being within the scope of the following claims particularly pointing out and distinctly claiming the subject matter regarded as the invention.

I claim:

1. A filling system including an anesthetic storage container and a drug reservoir, the filling system for use in transferring an anesthetic liquid between the anesthetic storage container and the drug reservoir, the filling system comprising:
   a filling device coupled to the drug reservoir to receive the anesthetic storage container;
   at least one filling conduit formed in the filling device, the filling conduit having a first end including a flow opening in communication with the drug reservoir and a second end coupled to the anesthetic storage container, the filling conduit providing a pathway for both the anesthetic liquid from the anesthetic storage container and a replenishment gas to flow between the anesthetic storage container and the drug reservoir; and
   a closing valve operatively positioned adjacent to the flow opening of the filling conduit, the closing valve being movable to a closed position when a level of the anesthetic agent in the drug reservoir exceeds a desired level, whereby when the closing valve is in the closed position, the closing valve prevents the flow of anesthetic agent from the anesthetic storage container into the drug reservoir.

2. The filling system of claim 1 wherein the closing valve includes a float positioned in the drug reservoir, the float member being movable along with the level of the anesthetic liquid in the drug reservoir.

3. The filling system of claim 2 wherein the float is pivotally mounted for movement in the drug reservoir.

4. The filling system of claim 1 wherein the closing valve includes a sealing ring positioned to seal the flow opening and prevent the flow of anesthetic agent through the flow opening when the level of the anesthetic agent in the drug reservoir exceeds the desired level.

5. The filling system of claim 4 wherein the sealing ring is coupled to a float positioned in the drug reservoir, wherein the float moves along with the level of the anesthetic liquid in the drug reservoir such that the sealing ring seals the flow opening when the level of anesthetic agent in the drug reservoir exceed the desired level.

6. The filling system of claim 5 wherein the position of the sealing ring relative to the float is adjustable.

7. The filling system of claim 6 wherein the sealing ring is mounted to a support shaft, the support shaft being coupled to the float and extending through the flow opening.

8. The filling system of claim 7 wherein the sealing ring is positioned on the opposite side of the flow opening from the float such that the float pulls the sealing ring into contact with the flow opening when the level of the anesthetic liquid rises in the drug reservoir.

9. The filling system of claim 6 wherein the length of the support shaft extending from the float is adjustable.

10. A filling system including an anesthetic storage container and a drug reservoir, the filling system for use in transferring an anesthetic liquid between the anesthetic storage container and the drug reservoir, the filling system comprising:
    a filling device coupled to the drug reservoir to receive the anesthetic storage container;
    at least one filling conduit formed in the filling device, the filling conduit having a first end including a flow opening in communication with the drug reservoir and a second end coupled to the anesthetic storage container, the filling conduit providing a pathway for both the anesthetic liquid from the anesthetic storage container and a replenishment gas to flow between the anesthetic storage container and the drug reservoir;
    a closing valve operatively positioned adjacent to the flow opening of the filling conduit, the closing valve including a float pivotally mounted within the drug reservoir, the float being movable along with the fluid level of the anesthetic agent within the drug reservoir; and
    wherein the closing valve further comprises a sealing ring coupled to the float and positioned to block the flow opening when the fluid level in the drug reservoir exceeds a selected level.

11. The filling system of claim 10 wherein the position of the sealing ring relative to the float is adjustable.

12. The filling system of claim 11 wherein the sealing ring is mounted to a support shaft coupled to the float, wherein the length of the support shaft extending from the float is adjustable.

13. The filling system of claim 12 wherein the support shaft extends through the flow opening such that the sealing ring is positioned on the opposite side of the flow opening from the float such that the float pulls the sealing ring into contact with the flow opening when the level of the anesthetic liquid rises in the drug reservoir.

* * * * *